United States Patent [19]

Seddon et al.

[11] Patent Number: 4,675,460
[45] Date of Patent: Jun. 23, 1987

[54] PROCESS

[75] Inventors: Duncan Seddon, Mount Eliza; Sandra Bessell, Springvale South, both of Australia

[73] Assignee: The Broken Hill Proprietary Company Limited; Commonwealth Scientific & Industrial Research Organization, both of Campbell, Australia

[21] Appl. No.: 818,402

[22] Filed: Jan. 13, 1986

Related U.S. Application Data

[63] Continuation of Ser. No. 726,917, Apr. 24, 1985, abandoned, which is a continuation of Ser. No. 578,809, Feb. 10, 1984, abandoned.

[30] Foreign Application Priority Data

Feb. 11, 1983 [AU] Australia ............................... PF7990

[51] Int. Cl.$^4$ ........................... C07C 2/00; C07C 2/02
[52] U.S. Cl. .................................. 585/329; 585/517; 585/527; 585/529; 585/532; 585/533
[58] Field of Search ............... 585/329, 517, 527, 529, 585/532, 533

[56] References Cited

U.S. PATENT DOCUMENTS

| | | | |
|---|---|---|---|
| 3,972,832 | 8/1976 | Butter et al. | 585/533 |
| 4,239,927 | 12/1980 | Brennan et al. | 585/532 |
| 4,357,233 | 11/1982 | Dwyer et al. | 585/533 |
| 4,394,251 | 7/1983 | Miller | 585/533 |
| 4,414,423 | 11/1983 | Miller | 585/517 |

FOREIGN PATENT DOCUMENTS

| | | |
|---|---|---|
| 26041 | 4/1981 | European Pat. Off. . |
| 31675 | 7/1981 | European Pat. Off. . |
| 37671 | 10/1981 | European Pat. Off. . |
| 961319 | 6/1964 | United Kingdom . |
| 1009943 | 11/1965 | United Kingdom . |
| 1074129 | 6/1967 | United Kingdom . |
| 1245349 | 9/1971 | United Kingdom . |
| 1365317 | 8/1974 | United Kingdom . |
| 2034350 | 6/1980 | United Kingdom . |

*Primary Examiner*—Curtis R. Davis
*Attorney, Agent, or Firm*—Murray and Whisenhunt

[57] ABSTRACT

Gasoline capable of further processing into diesel fuel is produced by catalytic conversion of lower olefins, using a zeolite catalyst which has been modified by substituting a significant portion of the cation sites thereof by basic cations. A preferred catalyst comprises a zeolite and a binder, said catalyst containing at least 0.2% by weight of exchangeable basic cations. The gasoline so produced is readily converted by contact with a Friedel Crafts catalyst into a hydrocarbon product having a significant fraction boiling in the distillate range.

16 Claims, No Drawings

PROCESS

This application is a continuation of application Ser. No. 726,917 filed Apr. 24, 1985, now abandoned, which is a continuation of Ser. No. 578,809 filed Feb. 10, 1984, now abandoned.

This invention relates to the production of distillate (diesel fuel).

In accordance with the invention it has been unexpectedly found that gasoline feedstocks prepared in a particular manner can be readily processed into a hydrocarbon product with a significant fraction boiling in the distillate range.

The said gasoline feedstocks are prepared by conversion of light olefins, using a zeolite catalyst that is modified as hereinafter described.

The subsequent processing of the said gasoline feedstocks in accordance with the invention may be carried out using a conventional Friedel-Crafts catalyst.

The oligomerisation of light olefins over acid catalysts is well known—see e.g. Kirk-Othmer "Encyclopaedia of Chemical Technology" 3rd Edition 1978 John Wiley—Vol. 4. p. 362—this gives a material useful for gasoline blending stock. Higher severity oligomerisation to materials in the distillate range is possible, but the product, because of much skeletal isomerisation and branching, suffers from low cetane number e.g. tetra-iso-butylene-olefin oligomer of isobutylene, cetane No. 15, compared with n-hexadecane (cetane), cetane No. 100.

U.S. Pat. Nos. 3,894,106, 4,062,905 and 4,052,479 disclose the conversion of alcohols and ethers to higher hydrocarbons by contact with a zeolite catalyst having a silica to alumina ratio of at least 12 at about 260° to 450° C. The preferred zeolite catalysts have crystal densities which are not substantially below 1.6 grams per cubic centimeter. These special catalysts are exemplified by ZSM-12, as in West German Offenlegungsschrift No. 2,213,109, ZSM-21 and certain modified naturally occurring zeolites. The synthetic zeolites made using an organic cation are preferred.

Aromatization of hydrocarbon feedstocks over zeolites is well known. U.S. Pat. No. 3,760,024 discloses an aromatization process for a feedstock comprising $C_2$ to $C_4$ paraffins and olefins comprising contacting such a feedstock with crystalline aluminosilicates of the ZSM-5 family. U.S. Pat. No. 3,756,942 discloses contacting a feedstock having a boiling range of $C_5$ to about 250° F. with a crystalline aluminosilicate zeolite of the ZSM-5 type, and U.S. Pat. No. 4,150,062 describes an invention which relates to improved processing of light olefins of from 2 to 4 carbon atoms to product comprising high octane gasoline components. The process comprises contacting the olefin feedstock in the presence of co-fed water with a catalyst comprising a zeolite characterized by a silica/alumina molar ratio of at least 12.

The crystalline aluminosilicate zeolites used in the catalyst composition of the process of this latter invention are referred to generally as the ZSM-5 family, or as behaving like ZSM-5, and include ZSM-5, ZSM-11, ZSM-12, ZSM-35 and ZSM-38.

Olefin oligomerisation over zeolite of the ZSM-5 family such as ZSM-12 has also been described in U.S. Pat. No. 4,254,295. This disclosed a process for the selective oligomerization of linear and branched chain $C_2$ to $C_{12}$ olefins and comprised contacting the olefins, in the liquid phase, with a ZSM-12 zeolite at temperatures from about 80° F. to about 400° F. It was found that the process provided selective conversion of the olefin feed to oligomer products with high selectivity, the product containing little or no light cracked products, paraffins, etc.

Light olefins can be synthesised from alcohols such as methanol using zeolite catalysts similar to those described above, as in for example U.S. Pat. No. 4,025,576. This shows that a feed comprising one or more compounds selected from the lower monohydric alcohols with up to four carbon atoms, and their simple or mixed ether derivatives, at subatmospheric partial pressure, is completely converted to a mixture comprising mainly light olefins, by contact with a particular type of crystalline aluminosilicate catalyst.

Although it is a generally accepted fact that zeolites in the alkali metal form are of substantially less catalytic activity, in some cases completely inactive, the conversion of methanol over alkali metal modified zeolites has been described in U.S. Pat. No. 3,899,544. For conversion of alcohols and ethers to higher hydrocarbons by zeolite catalysts, if the zeolite is fully exchanged so that its cation content is substantially alkali metal, it loses most of its activity to catalyse this reaction. Such high alkali metal content zeolites do however retain activity for some catalytic roles, notably the dehydration of alcohols to ethers.

When most of the alkali metal is exchanged out of the zeolite and replaced by acid sites, (for example by ammonium exchange followed by calcination to liberate ammonia and leave a proton within the zeolite, or as in the case of acid stable zeolites such as ZSM-5, by direct exchange in acidic media) the catalyst is extremely active for converting alcohols and/or ethers to higher hydrocarbons. For example, in the conversion of methanol to hydrocarbons in contact with an H-ZSM-5 zeolite catalyst from which most of the alkali metal (usually sodium) has been removed, the hydrocarbon yield at 100% feed conversion is consistently about 44 weight percent, based upon methanol fed (i.e. little conversion to dimethyl ether and other oxygenates). Where none of the alkali metal has been removed the hydrocarbon yield is zero.

It is an object of the present invention to provide an improved process for the conversion of light olefins into a hydrocarbon stock a substantial portion of which boils in the distillate range with only a minor portion boiling in the gasoline range.

In accordance with and fulfilling this object, one aspect of this invention resides in the discovery that when the conversion of lower olefins, by which we mean $C_3$-$C_6$ olefins and mixtures thereof, to higher hydrocarbons, particularly hydrocarbons boiling in the gasoline boiling range, e.g. $C_5$ to 196° C., is carried out over a zeolite modified in a particular manner, the resulting gasoline can be readily processed, using for example a Friedel-Crafts catalyst, into a hydrocarbon stock with a significant fraction boiling in the distillate range. The conversion is carried out at about 100° C. to 450° C., preferably 300° to 450° C., up to about 50 atmospheres, and about 0.5 to 50 liquid hourly space velocity.

The catalyst modification which makes possible the improved operation described herein is to ensure that a significant portion of the cation sites of the aforementioned zeolite is occupied by basic cations, notably Lewis or Bronsted bases such as elements of Group Ia, IIa or Va of the Periodic table. Specific cations which have been found to be particularly useful are those which contain sodium, potassium, calcium, nitrogen and phosphorus, either alone or in appropriate cationic complex form.

The zeolites used as catalysts are usually obtained from a composition containing an organic cation. After initially producing the zeolite crystal structure desired with its original organic and alkali metal cations, it is dried, and then may be directly calcined, in which case the organic cations are removed by oxidation to produce a zeolite containing alkali metal cations. The alkali metal can be exchanged either with other metal ions or with ammonium ions or both. Where acid sites are desired ammonium cations are used. The ammonium form of the zeolite, upon calcination to remove ammonia, leaves the hydrogen form of the zeolite. The order of exchange and calcination is variable with several different sequences of operation reported to give special results for particular purposes well known in the art.

The catalyst of this invention can be prepared by converting all of the cationic sites to the alkali metal form and then exchanging a proportion of the alkali metal cations for acid or other "active" cations. Alternatively an acid form zeolite can be subjected to exchange with appropriate alkali metal moieties.

Another method of obtaining the catalyst of this invention is to mix the hydrogen (acid) form of the zeolite with a solid matrix or binder which has available alkalications. Although we do not wish to be limited by any theoretical or postulated mechanism for the observed beneficial results, we observe that, after the influence of calcination, the composite catalyst performs as if a portion of the zeolite component had been exchanged by alkali metal.

Another method of obtaining the catalyst of this invention is to use the as made zeolite; that is, a zeolite containing both organic and alkali metal cations, and calcining the zeolite (with or without binder, as powder or pellet) so as to remove a portion of the organic cations. It will be appreciated that the relative amount of organic and alkali-metal cation will be dependent on such things as the nature of the organic moiety, the relative concentrations of organic and alkali-metal in the synthesis-gel and to some extent the silica-alumina ratio of the zeolite, the relative proportion of which can be adjusted by methods well known to those skilled in the art. It will also be appreciated that in this embodiment, the catalyst is not subjected to ion exchange after synthesis (see examples 13, 20, 27 and 32 below).

Accordingly, the invention provides a process for conversion of lower olefins to hydrocarbons boiling in the gasoline boiling range, characterised in that the lower olefins are converted by contact with a zeolite catalyst which has been modified by substituting a significant portion of the cation sites thereof by basic cations, whereby the gasoline produced is capable of further processihg into a hydrocarbon product with a significant fraction boiling in the distillate range.

In a preferred embodiment of the invention the catalyst comprises a zeolite and a binder, said catalyst containing at least 0.2%, preferably at least 0.3%, of exchangeable basic cations, determined as oxide, on the total weight of the catalyst.

The catalyst may comprise up to 90% by weight binder, such as bentonite or alumina, but is preferably within the range of 25% to 75%.

The zeolite is preferably of the ZSM family, having an $Al_2O_3$ content of at least 1% by weight. Whilst the lower limits of alumina, and hence alkali metal, in the zeolite are determined by the need for sufficient catalytic activity, the upper limits are determined by the maximum level of zeolitic alumina that can be tolerated by a given zeolite. For example, it is well known that ZSM-5 will typically have maximum alumina contents at about 4.5% by weight; in this case the maximum alkali-metal content would correspond to about 80% of this value, calculated on a molar basis. Other zeolites can have much higher alumina contents, so that the corresponding maximum alkali content would be proportionally higher.

Those skilled in the art will realize that, on the basis of the above, the catalyst (zeolite plus binder) of the present invention preferably has 20% of the exchangeable basic cations on a molar basis relative to the alumina content of the zeolite. More preferably the figure is 30%.

In a further preferred embodiment of the invention a process for production of diesel fuel comprises the following steps:

(a) converting lower olefins at temperatures between about 100° to 450° C. preferably between 260° to 450° C. and more preferably between 300° and 450° C., pressures up to about 50 atmospheres, and LHSV of about 0.5 to 50hr$^{-1}$, in contact with a zeolite catalyst which has been modified by substituting a significant portion of the cation sites thereof by basic cations, preferably a catalyst comprising a zeolite and a binder, said catalyst containing at least 0.2%, and preferably at least 0.3%, of exchangeable basic cations, determined as oxide, on the total weight of the catalyst, to produce a first hydrocarbon product containing hydrocarbons boiling in the gasoline boiling range;

(b) converting the said first hydrocarbon product by contact with a Friedel-Crafts catalyst into a second hydrocarbon product a substantial portion of which boils in the distillate range with only a minor portion boiling in the gasoline range.

Preferably the second hydrocarbon product comprises at least 40%, and more preferably at least 50%, by weight distillate boiling at >235° C., and preferably less than 50%, and more preferably less than 40%, by weight gasoline.

It has been noted that a zeolite catalyst of this invention has alkali metal and acid cationic sites. It may also have other cationic sites, such as hydrogenation/dehydrogenation components, incorporated for given purposes. These other sites are to be considered as part of the acid site group and are not to be considered as replacing alkali metal cation moieties. These additional components can be incorporated with the zeolite catalyst by impregnation, vapor deposition or exchange, as may seem desirable.

It has been ascertained that the catalysts of this invention are capable of converting alcohols such as methanol into an olefinic gasoline, but the catalyst deactivates quickly, e.g. over a period of about five hours on line, making practical use of these catalysts for alcohol conversion difficult. Surprisingly, it has been found that olefin conversion over the catalysts continues to give useful yields of liquid product for much longer periods, e.g. greater than thirty hours on line before reactivation, by for example air-calcination, is required.

The present invention has further ascertained that the product hydrocarbon stock produced from olefins over alkali-metal containing zeolites such as described above can be easily converted by treatment with a Lewis acid catalyst such as aluminium chloride into a product rich in distillate fraction. The catalyst particularly useful for the conversion of the hydrocarbon stock can be termed a Friedel-Crafts catalyst, a detailed description of which can be found in "Friedel-Crafts and Related Reactions" G.A. Olah (ed) Vols 1-4, Interscience., 1963-65.

The invention will be further illustrated by the following non-limiting examples.

EXAMPLE 1

This example describes the synthesis of ZSM-5 with a high sodium content.

Aluminium wire (2.51 g) was dissolved in sodium hydroxide solution (15.2 g in 100 g water). The solution was then added to colloidal silica (667 g of Ludox HS40 (trade mark), 40% $SiO_2$) and stirred. Tetrapropylammonium bromide (147.8 g) in water (1000 g) was then added and the whole vigorously stirred to a homogeneous gel. The gel was stiffened by the addition of sodium chloride (250 g). The zeolite was crystallized from the mixture by heating the gel in an autoclave to 175° C., with stirring, for 16 hours. The zeolite was obtained from the mother liquor by filtration and washing with distilled water. The as-made zeolite was then washed with 2 M hydrochloric acid and then calcined (500° C. in moist air for 16 hrs.). The product analysed at 1.46% $Al_2O_3$ and 1.74% $Na_2O$ (i.e. all Al expressed as Wt % $Al_2O_3$ and all Na expressed as Wt % $Na_2O$).

EXAMPLE 2

This example describes a further synthesis of high sodium content ZSM-5.

The zeolite was prepared in an analogous manner to that described in Example 1 except that the weights of active components were: aluminium wire (1.28 g) sodium hydroxide (7.5 g); colloidal silica (336.6 g), tetra-n-propylammonium bromide (73.9 g). The same quantities of water and sodium chloride were used as for Example 1. After acid washing, calcination and drying, the product was analysed at 1.18% $Al_2O_3$ and 0.8% $Na_2O$.

EXAMPLE 3

This describes the conversion of propylene over high sodium ZSM-5.

Samples of zeolite from examples 1 and 2 were mixed with bentonite (33% by weight bentonite) and water, then extruded. The extrusions (3 mm) were dried and calcined at 500° C. They were then charged (72 g plus 40 g of inert alumina spheres) into a downflow tubular reactor. Propylene was passed at 36 liters/hr over the catalyst at about 300° C. and the liquid products condensed (123 g of liquid). The liquid was analysed by gas-chromatography (12.5 m, SP2100, fused silica column) and a simulated distillation profile obtained. The results are shown in Table 1 and indicate the product consists predominantly of material boiling in the gasoline-range.

TABLE 1

| Simulated Distillation Profile of Liquid Product from Example 3. | | |
|---|---|---|
| Fraction | Simulated Boiling Range | Wt % |
| gasoline | <196° C. | 93.4 |
| jet-fuel | 196-235° C. | 4.3 |
| middle distillate 1 | 235-317° C. | 1.7 |
| middle distillate 2 | >317° C. | 0.7 |

EXAMPLE 4

This describes the conversion of the liquid product obtained in Example 3 into material boiling in the distillate range.

The liquid (30 g) and anhydrous aluminium chloride (10 g) were refluxed (for 3 hours). The mixture was then hydrolysed by shaking with water (approx. 200 cc) and the hydrocarbon fraction obtained by separation and filtration. The liquid product was subjected to the same chromatographic analysis as in Example 3; the results of the simulated distillation profile are shown in Table 2 and clearly demonstrate the increase in boiling points obtained by $AlCl_3$ treatment.

TABLE 2

| Simulated Distillation Profile of Liquid Product from Example 4. | | |
|---|---|---|
| Fraction | Simulated Boiling Range | Wt % |
| gasoline | <196° C. | 28.6 |
| jet-fuel | 196-235° C. | 12.9 |
| middle distillate 1 | 234-317° C. | 27.8 |
| middle distillate 2 | >317° C. | 30.6 |

EXAMPLE 5

This describes the conversion of propylene over acid ZSM-5 (H-ZSM-5).

H-ZSM-5 was obtained by a preparation similar to that described in Example 1. The final product was converted into a low sodium form by further washing the product with 2 M hydrochloric acid, then giving the product a further calcination. The product was fabricated into extrudates (as described in Example 3) and used to convert propylene (25 L/hr over 47 g of catalyst at approx. 350° C.). The resulting liquid product (62 g) was subjected to the same gas-chromatographic analysis as described in Example 3. The results are shown in Table 3 and illustrate the product had a very similar boiling-point profile as the product of Example 3.

TABLE 3

| Simulated Distillation Profile of Liquid Product from Example 5. | | |
|---|---|---|
| Fraction | Simulated Boiling Range | Wt % |
| gasoline | <196° C. | 91.6 |
| jet-fuel | 196-235° C. | 5.7 |
| middle distillate 1 | 235-317° C. | 2.2 |
| middle distillate 2 | 317° C. | 0.5 |

EXAMPLE 6

The liquid product of Example 5 was then treated with aluminium chloride as hydrolysed as described in Example 4. The resultant liquid was again analysed by gas-chromatography and the simulated distillation profile obtained (Table 4). Comparison of Table 4 and 2 demonstrates the ineffectiveness of the Friedel-Crafts treatment in Example 6 in that the major portion of the product remains in the gasoline boiling-range.

TABLE 4

| Simulated Distillation Profile of the Product obtained from Aluminium Chloride Treatment of Liquid Product obtained from Example 5. | | |
|---|---|---|
| Fraction | Simulated Boiling Range | Wt % |
| gasoline | 196° C. | 76.9 |
| jet-fuel | 196-235° C. | 5.7 |
| middle distillate 1 | 235-317° C. | 4.6 |

TABLE 4-continued

Simulated Distillation Profile of the Product
obtained from Aluminium Chloride Treatment of Liquid
Product obtained from Example 5.

| Fraction | Simulated Boiling Range | Wt % |
|---|---|---|
| middle distillate 2 | 317° C. | 12.8 |

EXAMPLE 7-13

These examples describe the characteristics of catalysts usdd in following examples.

TABLE 5

| | | Zeolite Analysis | Catalyst Analysis (a) | | | |
|---|---|---|---|---|---|---|
| Example | Code | SiO2/Al2O3 (c) | % SiO2 | % Al2O3 | % Na2O | % Fe2O3 |
| 7 | A1 | 95 | 86.0 | 7.4 | 0.56 | (b) |
| 8 | A2 | 40 | 80.8 | 8.0 | 0.88 | (b) |
| 9 | A3 | 95 | 85.9 | 7.6 | 0.68 | 1.33 |
| 10 | A4 | 40 | 78.5 | 8.0 | 1.31 | 1.19 |
| 11 | A5 | 95 | 77.5 | 6.4 | 1.18 | 1.08 |
| 12 | A6 | 95 | 82.0 | 7.0 | 1.28 | 1.21 |
| 13 | A7 | 95 | 79.2 | 7.2 | 1.50 | 1.26 |

(a) analyses, on a weight basis, of a 2/1, zeolite/bentonite extrusion, expressing all metal as its oxide.
(b) not determined.
(c) molar.
(d) impurity in bentonite.

The zeolites were synthesised by crystallisation of silica/alumina gels using tetra-n-propylammonium cation as organic templating cation. They were modified to differing sodium content as illustrated in Table 5. In examples 7 and 8 the catalysts were made from the "as-made" zeolites by ion-exchanging with hydrochloric acid (2M) and calcining the catalyst twice. The sodium content of the zeolite before fabrication was very low. The zeolites were then mixed with bentonite (2/1, w/w) and formed into extrusions. For catalysts in Examples 9, 10, 11, the zeolites (from separate syntheses) were ion-exchanged and calcined only once. The catalyst of Example 12 was the same as Example 11, but was further washed with ammonium/sodium ion solution. The catalyst of Example 13 was the "as-made" zeolite i.e. received no ion-exchanges or calcinations before mixing with bentonite and forming into a catalyst. This illustrates the effect of leaving the tetra-n-propylammonium cations in the zeolite.

EXAMPLES 14-20

These examples illustrate the use of catalysts of Examples 7-13 to prepare gasolines of varying olefinic content. Propylene, at 1 atm. pressure, was passed over a packed bed of the catalyst held at 300° C. After cooling to ambient the product gasolines were collected and the quantity of aliphatics present determined by NMR and GLC, and the gasolines characterised by RON (clear). The results are given in Table 6.

TABLE 6

| Example | Catalyst | WHSV (hr$^{-1}$) | Max Temp (°C.), (a) | Liquid Yield (b) | I(A/O) (c) | % aliphatics (d) | RON (clear) |
|---|---|---|---|---|---|---|---|
| 14 | Ex 7 | 2.4 | 483 | 0.50 | 9.0 | 41.3 | 100.0 |
| 15 | Ex 8 | 1.5 | 455 | 0.47 | 4.7 | 53.5 | 98.6 |
| 16 | Ex 9 | 2.2 | 445 | 0.49 | 0.5 | 79.5 | 95.5 |
| 17 | Ex 10 | 1.6 | 449 | 0.59 | 1.7 | 80.9 | 96.8 |
| 18 | Ex 11 | 2.6 | 410 | 0.47 | 0.19 | 81.5 | 95.5 |
| 19 | Ex 12 | 2.8 | 433 | 0.34 | 0.20 | 83.3 | 92.3 |
| 20 | Ex 13 | 0.9 | 383 | 0.58 | 0.34 | 75.2 | |

(a) hot spot temperature.
(b) gg$^{-1}$ of propylene converted.
(c) Ratio of aromatic proton intensity/olefin proton intensity by $^1$H N.M.R.
(d) from G.L.C.

Examples 14 and 15 illustrate that extensive exchange of the zeolite to remove alkali-cation results in higher aromatic content gasoline than if the zeolite is ion-exchanged and calcined just once (Examples 16-18). Example 19 illustrates that excessive back exchange with sodium ions may reduce unduly the activity of the catalyst (liquid yield ~0.34 gg$^{-1}$ propylene fed). Example 20 illustrates that "as-made" catalysts which may retain significant portions of alkyl quaternary cations and/or their decomposition products are effective catalysts. It should be noted that all products were acceptable as gasolines of high (>90) RON (clear).

EXAMPLES 21-27

These illustrate the conversion of the gasolines described in Examples 14-20 into products boiling greater than 196° C.

Samples of gasolines described in Examples 14-20 were treated with anhydrous aluminium chloride under reflux conditions. After three hours the reaction was stopped by adding water. The organic phase was separated and analysed by a G.L.C. simulated distillation technique and by N.M.R. The results are given in Table 7.

TABLE 7

| Example | Product From | I(A/O) | Product B.P. (simulated distillation) | | | |
|---|---|---|---|---|---|---|
| | | | <196 °C. | 196-235 °C. | 235-317 °C. | >317 °C. |
| 21 | Ex 14 | 6.8 | 69.4 | 10.0 | 9.3 | 11.3 |
| 22 | Ex 15 | 2.7 | 51.2 | 10.0 | 16.3 | 22.5 |
| 23 | Ex 16 | 0.4 | 49.1 | 8.4 | 20.2 | 22.4 |
| 24 | Ex 17 | 0.4 | 45.1 | 17.0 | 22.4 | 15.6 |
| 25 | Ex 18 | 0.3 | 25.6 | 12.2 | 29.6 | 32.6 |
| 26 | Ex 19 | 0.4 | 33.6 | 8.7 | 25.1 | 32.6 |
| 27 | Ex 20 | 0.3 | 30.3 | 11.1 | 27.0 | 31.6 |

Although all the gasoline feedstocks gave some products higher in boiling point than gasoline (<196° C.), the products of Examples 21 and 22 in which the zeolite had received multiple ion exchange and calcination were inferior to the other products. Although Example 23 is similar to 22, the performance in the former case is preferred because more product in the middle distillate range (235°-317° C.) is obtained. These examples serve to illustrate that good yields of middle distillate and higher products can be obtained from propylene by using catalysts of high exchangeable alkali-content, and that excessive removal of the alkali by ion-exchange hinders the production of distillate boiling products (Examples 21 and 22).

From the above it will be evident that preferred catalysts are represented by Examples 1, 2, 9, 10, 11 and 13.

EXAMPLES 28, 29

These examples serve to illustrate the effect of on-stream time on the conversion of propylene to gasoline over the alkali-metal containing zeolites.

The results are given in Table 8. As can be seen the performance of both catalysts changes with time-on-stream, but the preferred catalyst (Example 29) is that one containing a zeolite with only one ion-exchange treatment and where the change in performance is less severe. Both catalysts produce high yields of aromatics at early time on line but for the preferred catalyst, this aromatic yield rapidly falls to a very low value within 340 min. on-stream-time.

TABLE 8

| Time on-stream (min) | Max Temp (°C.) | Liquid Yield (gg$^{-1}$ propene converted) | I(A/O) | % Aliphatics |
|---|---|---|---|---|
| Example 28 Catalyst Ex-8, WHSV = 1.1 hr$^{-1}$ | | | | |
| 190 | 455 | 0.41 | 17.6 | 33 |
| 309 | 449 | 0.51 | 6.1 | 46 |
| 509 | (424) | 0.57 | 1.8 | 49 |
| 751 | 433 | 0.53 | 1.2 | 60 |
| 996 | 452 | 0.39 | 0.8 | 67 |
| 1212 | 447 | 0.41 | 0.6 | 66 |
| Example 29 Catalyst Ex-10, WHSV = 1.6 hr$^{-1}$ | | | | |
| 180 | 449 | 0.54 | 8.6 | 45.0 |
| 340 | 437 | 0.65 | 0.4 | 71.0 |
| 475 | 423 | 0.65 | 0.1 | 90.0 |
| 610 | 424 | 0.64 | 0.2 | 83.5 |
| 820 | 416 | 0.61 | 0.3 | 87.6 |
| 920 | 413 | 0.59 | 0.3 | 90.6 |
| 1105 | 398 | 0.49 | 0.01 | 89.4 |
| 1260 | 392 | 0.47 | 0.01 | 90.8 |

EXAMPLE 30, 31

These illustrate the conversion of butylenes over the preferred catalyst as described in Example 9. The results are given in Table 9. These results show that light olefins such as 1-butene and isobutene can be converted to olefinic gasoline over the alkali-metal containing catalysts.

Experiments using ethylene failed to give significant yields of gasolines under similar conditions.

TABLE 9

| Time On-Line (min) | Max Temp (°C.) | Liquid Yield (gg$^{-1}$ 1-butene converted) | I(A/O) | % Aliphatics |
|---|---|---|---|---|
| Example 30 1-Butene Feed WHSV = 1 hr$^{-1}$ | | | | |
| 180 | 366 | .64 | 0.5 | 76.4 |
| 335 | 361 | .76 | 0.2 | 74.6 |
| 470 | 359 | .77 | 0.2 | 76.4 |
| 528 | 358 | .73 | 0.1 | 79.1 |
| 718 | 354 | .78 | 0.1 | 77.7 |

| Time On Line (min) | T °C. (max) | Liquid Yield (gg$^{-1}$ isobutene converted) | I(A/O) | % Aliphatics |
|---|---|---|---|---|
| Example 31 Isobutene Feed WHSV = 1 hr$^{-1}$ | | | | |
| 150 | 348 | .64 | 0.4 | 70.9 |
| 290 | 344 | .73 | 0.2 | 75.8 |
| 445 | 342 | .73 | 0.1 | 78.6 |
| 595 | 340 | .72 | 0.1 | 78.4 |
| 760 | 340 | .80 | 0.1 | 77.7 |
| 970 | 340 | .71 | 0.08 | 78.2 |
| 1270 | 340 | .78 | 0.07 | 80.4 |

TABLE 9-continued

| 1425 | 325 | .64 | 0.07 | 80.1 |

EXAMPLE 32

This illustrates the beneficial use of potassium as alkali-metal to influence the performance of the zeolite.

A catalyst was formed in a similar manner to that described in Example 13 except in that the starting gel contained only potassium as the alkali-metal.

Reaction with propylene, in a similar manner to that described in Example 20, gave a gasoline of very low aromatic content (I(A/O) <0.1) with a RON (clear) of 96.1.

EXAMPLE 33 and 34

These illustrate that alkaline earth cations of Group IIa beneficially produce an olefinic gasoline but those of Group IIb give an aromatic gasoline.

Zeolites similar to those described in Examples 7 and 1 were treated with calcium and zinc exchange solutions respectively. After exchange and forming into extrusions (2/1, zeolite/bentonite) the catalysts contained 3.50% CaO and 0.77% ZnO respectively.

Propylene was passed over the catalysts in a similar manner to that described for Example 14-20. The results are given in Table 10.

TABLE 10

| Example | Exchange Cation | WHSV (hr$^{-1}$) | T °C. (max) | Yield[a] | I(A/O) |
|---|---|---|---|---|---|
| 33 | Ca | 0.9 | 412 | 0.50 | 0.36 |
| 34 | Zn | 1.84 | 267 | 0.42 | 0.63 |
| | | | 466 | 0.22 | 16.7 |

[a] g.g.$^{-1}$ of propylene fed, average value.

The calcium treated zeolite (Example 33) gives an olefinic gasoline with acceptable yield. The zinc treated catalyst (Example 34) appears only useful at low temperatures, higher temperatures giving higher yields of aromatics.

EXAMPLES 35-42

These examples serve to illustrate that olefinic gasolines produced by the preferred catalysts can be converted, by a variety of catalysts, into a product containing significant quantities of kerosene, distillate and fuel-oil. The results are shown in Table 11, where an olefinic gasoline feed was obtained from propylene using the catalyst described in Example 9.

From the results, aluminium chloride, boron trifluoride on silica-alumina, aluminium chloride on silica-alumina, and phosphoric acid on kieselguhr gave reasonable yields of products higher in boiling point than gasoline. Hydrogen fluoride treated silica-alumina gave somewhat lower yields, as did the zeolite of Example 42.

These results illustrate that distillate range products can be produced from the olefinic gasolines described above by a wide variety of solid-acid catalysts, as well as homogeneous catalysts such as aluminium chloride.

TABLE 11

| | | Simulated Distillation | | | |
|---|---|---|---|---|---|
| Catalyst | Treatment | Gasoline | Kerosene | Distillate | Fuel Oil |
| — | Starting | Nil | 91.6 | 3.4 | 3.6 | 1.4 |

TABLE 11-continued

| Catalyst | Treatment | Simulated Distillation | | | |
|---|---|---|---|---|---|
| | | Gasoline | Kerosene | Distillate | Fuel Oil |
| Ex 35 Gasoline AlCl₃ | Reflux 180 mins. 25 wt. % AlCl₃ | 45.5 | 13.8 | 32.5 | 8.2 |
| Ex 36 BF₃ on Silica-alumina | 130° C. overnight 25 wt. % catalyst | 55.3 | 11.5 | 21.4 | 11.8 |
| Ex 37 BF₃ on Silica-alumina | 130° C. overnight 12.5 wt. % catalyst | 62.6 | 11.5 | 17.1 | 8.9 |
| Ex 38 AlCl₃ on silica-alumina | 130° C. overnight 25 wt. % catalyst | 68.6 | 10.4 | 13.9 | 7.2 |
| Ex 39 H₃PO₄ on kieselguhr | 130° C. overnight 25 wt. % catalyst | 80.0 | 10.6 | 7.6 | 1.8 |
| Ex 40 HF on silica-alumina | 130° C. overnight 25 wt. % catalyst | 84.8 | 7.4 | 5.6 | 2.3 |
| Ex 41 BF₃, HF on silica-alumina | 130° C. overnight 25 wt. % catalyst | 87.1 | 6.1 | 4.6 | 2.3 |
| Ex 42 Example 7 | 130° C. for 5 hours 25 wt. % catalyst | 87.3 | 5.0 | 4.8 | 2.9 |

EXAMPLE 43

This example illustrates that methanol conversion over the preferred catalyst is unstable, and conversion can only be maintained for a limited on-stream-time.

A down flow reactor was charged with 70 g of a catalyst formed as in Example 9. Methanol (at WHSV ~2.1 hr$^{-1}$) was passed over the catalyst at 360° C. A hot-spot developed near the top of the bed, reaching 564° C. After five hours on stream the hot spot had travelled to the bottom of the bed indicating deactivation of the catalyst. It is well known that conversion falls to very low levels when the hot spot is lost from the catalyst bed, hence the effective useful on-stream-time for methanol conversion was only 5 hours.

EXAMPLE 44

This example illustrates the conversion of dimethylether (DME) over a high sodium catalyst.

Dimethylether (1000 ml min$^{-1}$) was passed over a catalyst (70 g) as described in Example 43. The details of the conversion are given in Table 12.

TABLE 12

| Time on line (min cumulative) | Set Temp. (°C.) | Max Temp (°C.) | % DME in gas phase products (a) | Hot spot position |
|---|---|---|---|---|
| 60 | 350 | 547 | nil | top of bed |
| 300 | 350 | 572 | 1.8 | bottom of bed |
| 420 | 400 | 566 | 6.9 | middle of bed |
| 660 | 475 | 579 | 1.1 | bottom of bed |
| 750 | 475 | 557 | 54.4 | bottom of bed |

(a) Liquid products condensed out at ambient temperature.

These results illustrate that the preferred catalysts, although capable of converting dimethylether, can only do so for a limited time on-line and that increasing the bed temperature fails to overcome the activity decay. This is in contrast to conversion of light olefins, propylene, butylene etc., which are able to undergo conversion for much longer periods before regeneration is required.

It will be clearly understood that the invention in its general aspects is not limited to the specific details referred to hereinabove.

We claim:

1. A process for the production of diesel fuel comprising:
    converting lower olefins into gasoline by contacting said lower olefins with a zeolite catalyst;
    converting said gasoline into a hydrocarbon product, having a portion thereof boiling in the distillate range, by contacting said gasoline with a Friedel-Crafts catalyst;
    separating diesel fuel from said hydrocarbon product;
    wherein said zeolite catalyst is a ZSM-5, a ZSM-11 or a ZSM-12 catalyst having cation sites which has been modified by substituting a portion of said cation sites by at least one basic cation selected from the group consisting of potassium, sodium and calcium.

2. A process for conversion of lower olefins to diesel fuel comprising:
    contacting said lower olefins with a first catalyst to converter said lower olefins into gasoline;
    contacting said gasoline with a second catalyst to convert said gasoline into a hydrocarbon product containing diesel fuel;
    separating said diesel fuel from said hydrocarbon product;
    wherein said first catalyst comprises a zeolite and a binder and contains at least 0.2% by weight of exchangeable basic cations, determined as oxide on the total weight of the catalyst, said cations being at least one member selected from the group consisting of potassium, sodium and calcium.

3. The process according to claim 2, wherein said first catalyst contains at least 0.3% by weight of exchangeable basic cations, determined as oxide on the total weight of the catalyst.

4. The process according to claim 3, wherein said first catalyst includes alkali metal and acid cationic sites.

5. The process according to claim 2, wherein said first catalyst includes alkali metal and acid cationic sites.

6. A process for the production of diesel fuel comprising:
    (a) converting lower olefins to a first hydrocarbon product containing hydrocarbons boiling in the gasoline boiling range by contacting said lower olefins with a zeolite catalyst;
    (b) converting said first hydrocarbon product to a second hydrocarbon product having a portion which boils in the distillate range by contacting said first hydrocarbon product with a second catalyst; and
    (c) separating diesel fuel from said second hydrocarbon product;
    wherein said conversion of said lower olefins is effected at a temperature between about 100° and 450° C., at a pressure up to about 50 atmospheres, and at an LHSV of about 0.5 to hr$^{-1}$, and wherein said zeolite catalyst has cationic sites which have been modified by substituting a portion of said cation sites with at least one basic cation selected from the group consisting of potassium, sodium and calcium.

7. The process for the production of diesel fuel according to claim 6, wherein said zeolite catalyst comprises a zeolite and a binder, said catalyst containing at least 0.2% of exchangeable basic cations, determined as oxide on the total weight of the catalyst.

8. The process for the production of diesel fuel according to claim 7, wherein said zeolite catalyst contains at least 0.3% of exchangeable basic cations, determined as oxide on the total weight of the catalyst.

9. The process for the production of diesel fuel according to claim 6, wherein said zeolite is of the ZSM family having an $Al_2O_3$ content of at least 1.0% by weight.

10. The process according to claim 2, wherein said zeolite is of the ZSM family having an $Al_2O_3$ content of at least 1.0% by weight.

11. The process for the production of diesel fuel according to claim 9, wherein said zeolite is ZSM-5, ZSM-11 or ZSM-12.

12. The process according to claim 10, wherein said zeolite is ZSM-5, ZSM-11 or ZSM-12.

13. The process for the production of diesel fuel according to claim 7, wherein said binder comprises up to 90% by weight of said zeolite catalyst.

14. The process for the production of diesel fuel according to claim 8, wherein said binder comprises up to 90% by weight of said zeolite catalyst.

15. The process for the production of diesel fuel according to claim 11, wherein said second catalyst is a Friedel-Crafts catalyst.

16. The process according to claim 12, wherein said second catalyst is a Friedel-Crafts catalyst.

* * * * *